United States Patent
Lustig

(10) Patent No.: US 8,150,632 B2
(45) Date of Patent: *Apr. 3, 2012

(54) METHOD FOR THE SELECTION OF AN OPERATIVE COMPONENT FOR AMALGAMATING A MULTIPLE PHASE SYSTEM INTO A SINGLE PHASE SYSTEM, DISPERSION OR EMULSION

(75) Inventor: Steven Raymond Lustig, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 644 days.

This patent is subject to a terminal disclaimer.

(21) Appl. No.: 12/257,548

(22) Filed: Oct. 24, 2008

(65) Prior Publication Data
US 2009/0112546 A1  Apr. 30, 2009

Related U.S. Application Data

(60) Provisional application No. 61/000,567, filed on Oct. 26, 2007, provisional application No. 61/000,580, filed on Oct. 26, 2007, provisional application No. 61/000,526, filed on Oct. 26, 2007, provisional application No. 61/000,516, filed on Oct. 26, 2007, provisional application No. 61/000,452, filed on Oct. 26, 2007, provisional application No. 61/000,536, filed on Oct. 26, 2007, provisional application No. 61/000,534, filed on Oct. 26, 2007.

(51) Int. Cl.
*G01N 33/48* (2006.01)
*G01N 31/00* (2006.01)
*G01N 33/50* (2006.01)
*G06F 7/60* (2006.01)

(52) U.S. Cl. ............... 702/19; 702/22; 702/23; 702/25; 703/2

(58) Field of Classification Search ................ None
See application file for complete search history.

(56) References Cited

U.S. PATENT DOCUMENTS
2004/0052898 A1 * 3/2004 Yatka et al. ................ 426/3

OTHER PUBLICATIONS

Carr et al. Temperature-induced changes in reversed-phase chromatography surfaces: C8 and C9 polymeric ligands. Journal of Chromatography, vol. 481, 1989, pp. 135-146.*
Gibbs energy, 2009. The Penguin Dictionary of Science, one page. Retrieved online on Apr. 13, 2011 <<http://www.credoreference.com/entry/penguinscience/gibbs_energy_gibbs_free_energy_gibbs_function>>.*

(Continued)

*Primary Examiner* — Russell S Negin

(57) ABSTRACT

A method for selecting an operative component to combine first and second immiscible phases includes selecting a first operative component and computing the value of the free energy of mixing for it and the first and second immiscible phases. If the computed free energy is greater than zero, the sigma profile of the first candidate is mutated to define a hypothetical sigma profile of a candidate substitute operative component. The free energy of mixing for the substitute and the first and second immiscible phases is computed. The mutation and computation are repeated for a predetermined number of repetitions or until the free energy of the candidate substitute component and the first and second phases is less than zero, whichever first occurs. A material exhibiting a sigma profile corresponding to that of the candidate substitute producing a free energy of solvation less than zero is selected.

3 Claims, 4 Drawing Sheets

OTHER PUBLICATIONS

Emulsion, 1992. Academic Press Dictionary of Science and Technology, one page. Retrieved online on Apr. 13, 2011 <<http://www.credoreference.com/entry/apdst/emulsion>>.*

Duvedi et al., "Designing Environmentally Safe Refrigerants Using Mathematical Programming", Chemical Engineering Science, 1996, pp. 3727-3739, vol. 51.

Raman et al., "Optimization In Product Design With Properties Correlated With Topological Indices", Computers Chem. Engng, 1998, pp. 747-763, vol. 22.

Vaidyanathan et al., "Computer-Aided Synthesis Of Polymers And Blends With Target Properties", Ind. Eng. Chem. Res., 1996, pp. 627-634, vol. 35.

Eckert et al., "Fast Solvent Screening Via Quantum Chemistry: COSMO-RS Approach", AIChE Journal, Feb. 2002, pp. 369-385, vol. 48.

Delley et al., "An All-Electron Numerical Method For Solving The Local Density Functional For Polyatomic Molecules", Journal of Chemical Physics, Jan. 1, 1990, pp. 508-517, vol. 92.

Delley et al., "From Molecules To Solids With the DMol3 Approach", Journal of Chemical Physics, Nov. 8, 2000, pp. 7756-7764, vol. 113, No. 18.

Treutler et al., "Efficient Molecular Numerical Integration Schemes", J. Chem Physics, Jan. 1995, pp. 346-354, vol. 102.

Eichkorn et al., "Auxiliary Basis Sets to Approximate Coulomb Potentials", Chemical Physics Letters, vol. 240, Jun. 30, 1995, pp. 283-290. Revised Sep. 1, 1995, Chemical Physics Letters 242, pp. 652-660.

Eichkorn et al., "Auxiliary Basis Sets For Main Row Atoms And Transition Metals And their Use to Approximate Coulomb Potentials", Theoretical Chemistry Accounts, 1997, pp. 119-124, vol. 97.

Klamt et al., COSMO-RS: A Novel And Efficient Method For The Priori Prediction Of Thermophysical Data Of Liquids, Fluid Phase Equilibria, 2000, pp. 43-72, vol. 172.

Venkatasubramanian et al., "Genetic Algorithmic Approach For Computer-Aided Molecular Design", Chapter 28 from ACS Symposium Series, Computer-Aided Molecular Design: Applications in Agrochemicals, Materials, and Pharmaceuticals, Reynolds et al. Editors, American Chemical Society, Washington, DC, 1995, pp. 396-414.

Klamt et al., COSMO-RS From Quantum Chemistry to Fluid Phase Thermodynamics and Drug Design, Elsevier, 2005, Relevant pages include pp. 49-58; 83-87; and 109-115, (book not included).

Schreiber et al, "Interaction of Barnase With Its Polypeptide Inhibitor Barstar Studied by Protein Engineering", Biochemistry, 1993, vol. 32, pp. 5145-5150.

Lee et al, "Barstar Is Electrostatically Optimized for Tight Binding to Barnase", Nature Structural Biology, vol. 8, 2001, pp. 73-76.

Hartley R.W., "Directed Mutagenesis and Barnase-Barstar Recognition", Biochemistry, vol. 32, pp. 5978-5984, 1993.

* cited by examiner

METHOD FOR THE SELECTION OF AN OPERATIVE COMPONENT FOR AMALGAMATING A MULTIPLE PHASE SYSTEM INTO A SINGLE PHASE SYSTEM, DISPERSION OR EMULSION

This application claims the benefit of priority to the following seven (7) United States Provisional Applications:
61/000,567, filed Oct. 26, 2007
61/000,580, filed Oct. 26, 2007
61/000,526, filed Oct. 26, 2007
61/000,516, filed Oct. 26, 2007
61/000,452, filed Oct. 26, 2007
61/000,536, filed Oct. 26, 2007
61/000,534, filed Oct. 26, 2007

FIELD OF THE INVENTION

The present invention is, in general, directed to a method for selecting a substitute component.

CROSS REFERENCE TO RELATED APPLICATIONS

Subject matter disclosed herein is disclosed and claimed in the following copending applications, all filed contemporaneously herewith and all assigned to the assignee of the present invention:

A Method For The Selection Of A Substitute Component For A Modified Single Phase System Based Upon A Comparison With At Least One Predetermined Desired Property Of The Modified System;

A Method For The Selection Of A Substitute Component For A Single Phase System Based Upon A Comparison With At Least One Predetermined Property Of An Initial System;

A Method For The Selection Of A Substitute Component For A Modified Multiple Phase System Based Upon A Comparison With At Least One Predetermined Desired Property Of The Modified System;

A Method For The Selection Of A Substitute Component For A Multiple Phase System Based Upon A Comparison With At Least One Predetermined Property Of An Initial System;

A Method For The Selection Of A Substitute Component In A Single Component System; and A Method For Designing A Substitute Component For A Modified System.

REFERENCE TO COMPUTER PROGRAM LISTING APPENDIX

A computer program listing appendix is contained on each of two identical computer discs (respectively labeled "Copy 1" and "Copy 2") that are submitted with this application. The computer program listing appendix is hereby expressly incorporated by reference herein.

Each disc contains a single file named COSMOPAT.TXT
The file has a size in bytes of 69.8 KB.
The file was created on Oct. 25, 2007.

In addition, a paper copy of the program listing (pages A-1 through A-46) contained on each of the computer discs (written in ANSI C programming language) by which the present invention may be implemented is included herein following the description and preceding the claims. The paper copy of the program listing forms a part of this application.

DESCRIPTION OF THE PRIOR ART

The field of molecular design relates to the problem of creating a chemical system possessing certain desired properties by assembling atoms and groups of atoms into molecules. The creation of the molecules is performed using a generation algorithm while the properties are evaluated using predictive techniques linking molecular structure to properties.

The primary challenge in computer-aided molecular design is the accurate prediction of physical and chemical properties based on structural information and the efficient generation of structural alternatives.

Methods for generating molecules having specific physical properties have previously been reported by, for example, Duvedi and Achenie (A. P. Duvedi and L. E. K. Archenie, *Chem. Eng. Sci.,* 51, 3727, 1996), Venkatsubramanian et al. (V. Venkatasubramanian, K. Chan and J. M Caruthers, *ACS Symp. Series,* 589, 396, 1995), Raman and Maranas (V. S. Raman and C. D. Maranas, *Comp. Chem. Eng.,* 22, 747, 1998), Vaidyanathan and El-Halwagi (R. Vaidyanathan and M. El-Halwagi, *Ind. Eng. Chem. Res.,* 35, 627, 1996).

However most of the proposed methods create compounds containing limited structural information thereby restricting the range of property prediction methods that can be applied as well as making it difficult to distinguish between structural isomers.

The design of molecules is a complex process due to the size of the search space and the associated risk of encountering the so-called "combinatorial explosion" where the number of alternatives considered becomes so large that it is infeasible to solve the problem within a reasonable time frame with the available computational resources.

Harper and Gani (P. M. Harper and R. B. Gani, *AIChE Symp. Series,* 325, 176, 2001) developed a group contribution method which often successfully avoids combinatorial explosion. However, this method still relies on the assembly of three dimensional molecular structures from molecular fragments and prescreening these structures for a subset of properties. Further, this methodology is implementable for strict group-contribution methods, such as UNIFAC, which may have limited applicability to many kinds of chemicals and materials, particularly ionic liquids.

-o-0-o-

On the other hand, mathematical models of chemical systems and mixtures that predict thermodynamic properties such as vapor pressures, solubilities and activity coefficients have been in use for decades.

A recently developed mathematical model of a chemical mixture is the so-called conductor-like screening model (herein also referred to as "COSMO") described by A. Klamt and F. Eckert, *Fluid Phase Equilibria,* 2000, Vol 172, p 43; F. Eckert and A. Klamt, *AIChE Journal, February* 2002, Vol. 48 No. 2, pp. 369).

COSMO is a general and fast methodology for the a priori prediction of thermodynamic properties of chemicals. It is based on unimolecular quantum chemical calculations which, when combined with a Hamiltonian expression for interaction energy and exact statistical thermodynamics, provide the information necessary for the evaluation of thermodynamic properties.

A recent example of the COSMO methodology is provided in Andreas Klamt, *COSMO-RS: From Quantum Chemistry to Fluid Phase Thermodynamics and Drug Design,* Elsevier, N.Y. 2005. Software that implements the COSMO-RS methodology is available, e.g. COSMOthermX version C21_0106 by COSMOlogic GmbH & Co. KG (Burscheiderstr. 515, D-51381 Leverkusen, Germany).

An understanding of the rudiments of the COSMO methodology may be derived from the stylized pictorial drawings shown in FIGS. 1A through 1C.

COSMO calculations provide a discrete surface, approximating a surface of salvation, around each molecule embedded in a virtual conducting fluid (e.g., a solution). FIG. 1A is a stylized COSMO depiction of an individual solute molecule (such as formaldehyde, $CH_2O$) contained in the solution. The surface is indicated by the reference character S. In accordance with the COSMO methodology the surface S of the molecule may be represented as a plurality of individual ideal conductor surface segments, or charge tiles. Several of the tiles in FIG. 1A are indicated by the reference character T. Each tile T of this surface S has a predetermined area and carries a given polarization charge σ.

The polarization charge σ on any tile T results from the effect of the elemental descriptors of the molecule. Elemental descriptors may include the identity and character of the atom closest to the tile. "Identity" may include the atom's element and its valence state. "Character" may include the number of connected bonds, hybridization, the identity of neighboring atoms connected to those bonds, geometrical measures of the bonding such as bond distance, bond angle, torsions and any information about the system that affects the properties of the molecule containing that atom.

Polarization charge σ of a tile also takes into account the electrostatic screening of the solute molecule by its surroundings and the back-polarization of the solute molecule. The total energy of the ideally screened molecule is provided. Various software packages are available for this purpose. Among such available packages are:

"DMol3", available from Accelrys, Inc., San Diego, Calif.;
"Gaussian03", available from Gaussian Inc., Wallingford, Conn.; and
"Turbomole", available from Cosmologic GmbH & Co KG, Leverkusen, Germany.

Literature references for the "DMol3" software package include: B. Delley, *J. Chem. Phys.* 1990, 92, 508; and B. Delley, *J. Chem. Phys.* 2000, 113, 7756.

A literature reference for the "Gaussian03" software package is M. J. Frisch; G. W. Trucks; H. B. Schlegel; G. E. Scuseria; M. A. Robb; J. R. Cheeseman; J. A. Montgomery; Jr., T. V.; K. N. Kudin; J. C. Burant; J. M. Millam; S. S. Iyengar; J. Tomasi; V. Barone; B. Mennucci; M. Cossi; G. Scalmani; N. Rega; G. A. Petersson; H. Nakatsuji; M. Hada; M. Ehara; K. Toyota; R. Fukuda; J. Hasegawa; M. Ishida; T. Nakajima; Y. Honda; O. Kitao; H. Nakai; M. Klene; X. Li; J. E. Knox; H. P. Hratchian; J. B. Cross; C. Adamo; J. Jaramillo; R. Gomperts; R. E. Stratmann; O. Yazyev; A. J. Austin; R. Cammi; C. Pomelli; J. W. Ochterski; P. Y. Ayala; K. Morokuma; G. A. Voth; P. Salvador; J. J. Dannenberg; V. G. Zakrzewski; S. Dapprich; A. D. Daniels; M. C. Strain; O. Farkas; D. K. Malick; A. D. Rabuck; K. Raghavachari; J. B. Foresman; J. V. Ortiz; Q. Cui; A. G. Baboul; S. Clifford; J. Cioslowski; B. B. Stefanov; G. Liu; A. Liashenko; P. Piskorz; I. Komaromi; R. L. Martin; D. J. Fox; T. Keith; M. A. Al-Laham; C. Y. Peng; A. Nanayakkara; M. Challacombe; P. M. W. Gill; B. Johnson; W. Chen; M. W. Wong; C. Gonzalez; and J. A. Pople, *Gaussian* 03, *Revision C.*02, Gaussian Inc. Wallingford, Conn., 2004.

The "Turbomole" software package is discussed in papers by K. Eichkorn, O. Treutler, H. Oehm, M. Haeser and R. Ahlrichs (*Chemical Physics Letters* 242 (1995) 652-660); O. Treutler and R. Ahlrichs, *J. chem. Phys.* 102: 346 (1995); op cit., *Chem. Phys. Lett.* 240: 283 (1995); K. Eichkorn, O. Treutler, H. Oehm, M. Haeser and R. Ahlrichs, *Chem. Phys. Lett.* 242: 652 (1995); and K. Eichkorn, F. Weigend, O. Treutler and R. Ahlrichs, *Theo. Chem. Acc.* 97: 119 (1997).

From the polarization charges a sigma profile of the molecule may be constructed.

FIG. 1B is a graphical representation of the sigma profile of the molecule shown in FIG. 1A. As used herein the term "sigma profile" means the probability distribution of the polarization charge of the tiles T. It is a plot of the probability of a tile of the ideal conductor having a given charge versus the sign and magnitude of the given charge. Distributions of the elemental descriptors may be constructed and utilized as well. The sigma profile of the whole system/mixture is just a compositionally-weighted sum of the sigma profiles of the profiles of the individual components.

FIG. 1C is a stylized representation of a system, such as the solution containing the solute molecule of FIG. 1A, as viewed by the COSMO theory.

In accordance with COSMO theory the liquid solution is considered an ensemble of closely packed ideally screened molecules. In order to achieve this close packing the system has to be compressed and the surfaces of the molecules are, thus, slightly deformed. Each piece of a molecule's surface of salvation is in close contact with piece from the surface of salvation from another molecule.

In some regions the charge distribution on one molecule is equal and opposite of the charge distribution on the other molecule. A region of such ideal contact is indicated by the reference character I on FIG. 1C. However, in other regions the confronting charge tiles may not have equal and opposite charge densities. A region of electrostatic charge disparity is indicated by the reference character M on FIG. 1C. Interaction between such regions of electrostatic charge disparity imparts a net misfit energy to the system.

Taking into account such electrostatic misfit energy as well as contributions from other effects such as van der Waals interactions and hydrogen bonding interactions between surface of salvation segments (e.g., as indicated by the reference character H on FIG. 1C) the COSMO method generates an Hamiltonian expression for the overall interaction energy of the chemical system. The Hamiltonian energy expression involves only the polarization charges of the tiles and is independent of chemical group or molecular structure.

From the microscopic surface-interaction energies described by the Hamiltonian energy expression statistical thermodynamics may be used to calculate macroscopic thermodynamic properties of a chemical system. For example, the chemical potential of a surface segment can be calculated. Given the chemical potential for each segment, a molecule's chemical potential can be calculated. Knowing the chemical potentials of all molecules in the mixture, the total chemical potential of the mixture can be calculated. From this information other properties such as vapor pressure and activity coefficient can be calculated.

Since in the COSMO view all molecular interactions consist of local pairwise interactions of surface segments, the statistical averaging can be done in the ensemble of interacting surface pieces. Such an ensemble averaging is computationally very efficient, especially in comparison to conventional atomistic molecular dynamics or atomistic Monte Carlo approaches.

As discussed, to describe the composition of the surface segment ensemble with respect to the interactions, the probability distribution, the sigma profile, and possibly other elemental descriptors used in the Hamiltonian expression have to be known for all compounds. However, once given these parameters COSMO methodology is an efficient way to predict thermodynamic properties of a chemical system.

-o-0-o-

In view of the foregoing it is believed that it would be advantageous to provide a method that utilizes the more robust property predictive capabilities of COSMOO methodology when designing chemical systems that must exhibit certain predetermined desirable properties.

SUMMARY OF THE INVENTION

In accordance with the present invention COSMO methodology is used to select a substitute for one (or more) component(s) in an initial single or multiple phase system, where the substitute component(s) must exhibit one (or more) predetermined desired property(ies). The invention may be applied to an initial single component system or an initial multi-component system. The invention also has applicability to select an operative component to effect the combination of a first and a second phase into a single phase system, dispersion or emulsion. In addition to guiding the selection of such substitute component(s) from known available material(s), the method of the present invention may also be used to guide the design and/or synthesis of new substitute component(s).

In general, in accordance with the present invention, a mutation is introduced into the sigma profile of an existing component in a system thereby to define a hypothetical sigma profile of a candidate substitute component. The mutation may be effected by altering the polarization charge of a single charge tile or by altering the polarization charges on a collection of tiles, and/or by mutating one or more elemental descriptors of the initial component.

Using COSMO methodology the value of at least one selected property of a modified system containing the candidate substitute component is computed.

The modified system is evaluated to determine if it leads in the desired direction in terms of a specific property in question. The evaluation is based upon a comparison of the selected property of the modified system with a predetermined reference value. The predetermined reference value may be derived from a desired value a property of the modified system or the initial value of a property of the initial system.

Based upon the results of the comparison and using a predetermined acceptance standard the hypothetical sigma profile is accepted or, otherwise, any mutations effected to define the hypothetical sigma profile are discarded and the previous sigma profile is preserved.

The foregoing process steps are repeated using either the accepted sigma profile or the preserved sigma profile. Repetitions continue either for a predetermined number of times or until the value of the selected property of the modified system meets a predetermined finishing criterion, whichever first occurs. The finishing criterion may be satisfied, for example, if the property of the modified system meets or falls within a close range of the desired value or if the property of the modified system improves by a predetermined amount over the initial value.

A substitute component for a modified system is selected by identifying a material that exhibits a sigma profile corresponding to the mutated sigma profile of that trial substitute component that produces a modified system having a value of the selected property that meets the predetermined finishing criterion. A known component may be selected or a new component may be designed and synthesized.

BRIEF DESCRIPTION OF THE DRAWINGS

The invention will be more fully understood from the following description taken in connection with accompanying drawings, in which, FIGS. 1A through 1C are stylized pictorial drawings from which an understanding of the rudiments of the COSMO methodology may be derived, and in which:

FIG. 1A is a stylized COSMO depiction of an individual solute molecule (such as formaldehyde, $CH_2O$) contained in a solution;

FIG. 1B is a graphical representation of the sigma profile of the molecule shown in FIG. 1A; and FIG. 1C is a stylized representation of a system, such as the solution containing the solute molecule of FIG. 1A, as viewed by the COSMO theory.

DETAILED DESCRIPTION OF THE INVENTION

Figure 1A:
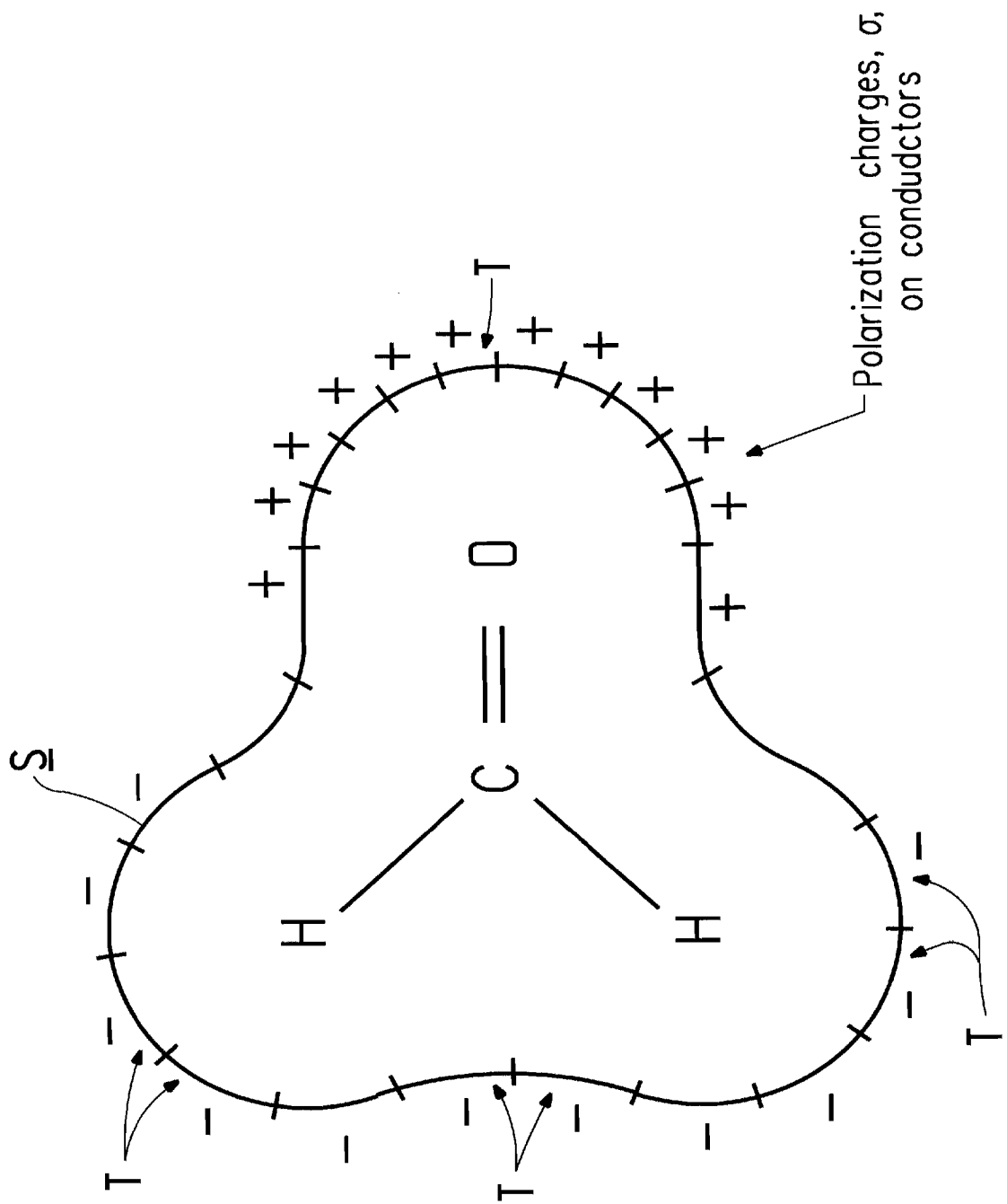
Figure 1B:
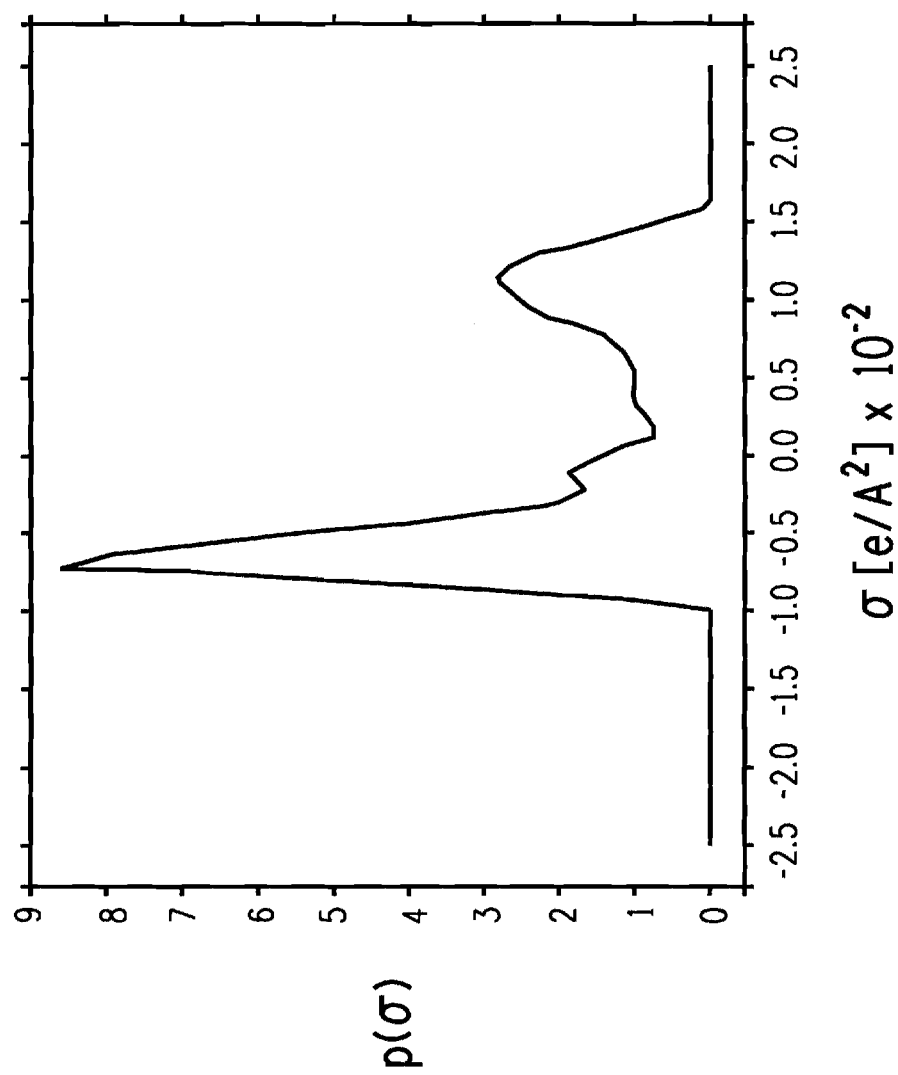
Figure 1C:
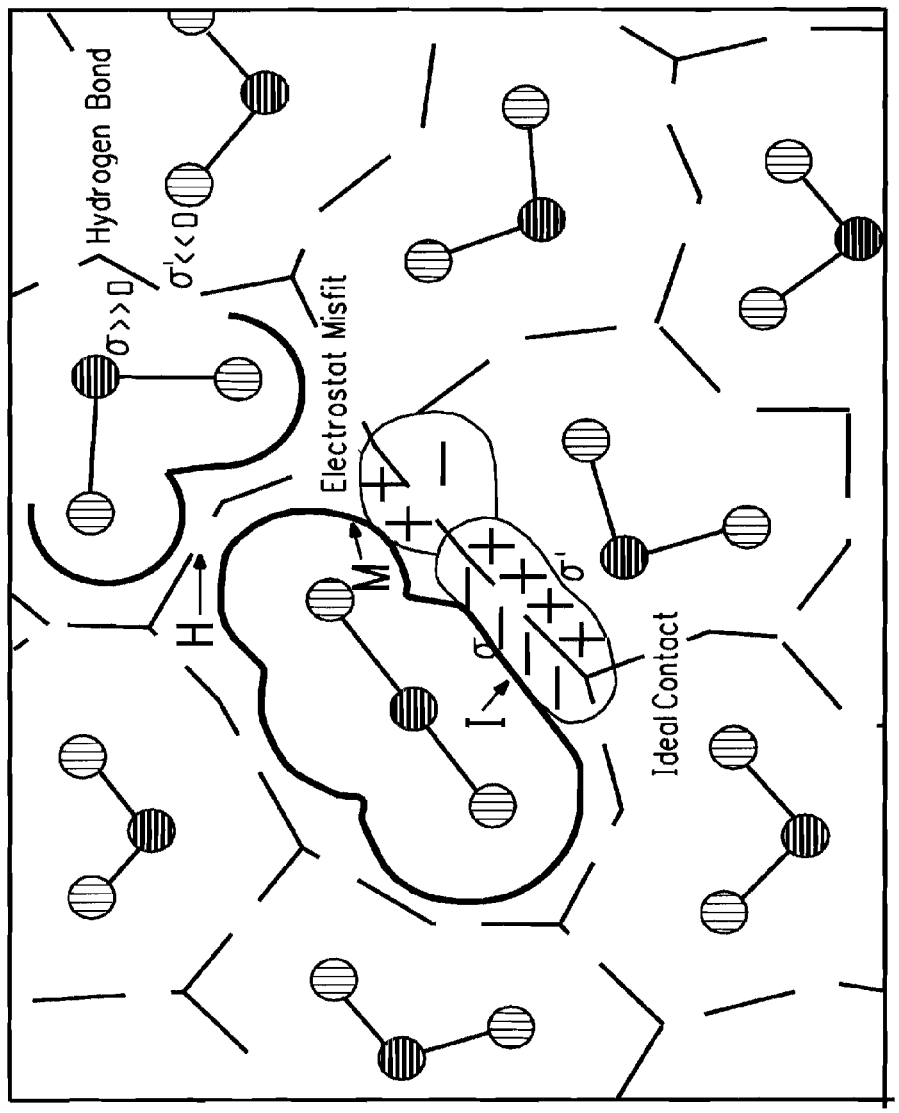

Throughout the following description similar reference numerals refer to similar elements in all Figures of the drawings.

Figure 2:
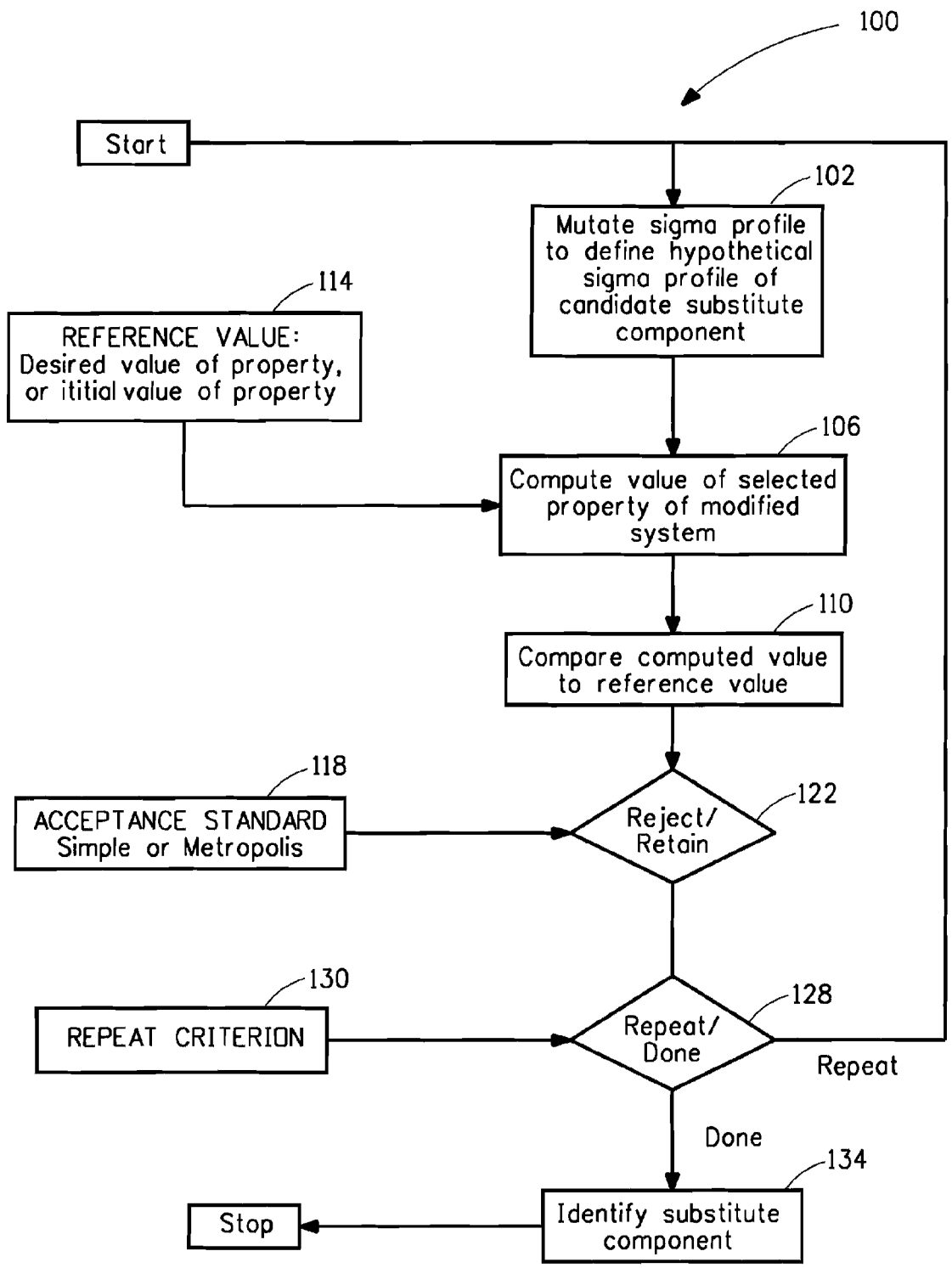
FIG. 2 is a flow diagram illustrating the generalized steps of a method in accordance with the present invention.

With reference to FIG. 2 shown is a flow diagram illustrating the generalized steps of a method indicated by reference character 100 in accordance with the present invention. As will be developed herein the method 100 uses COSMO methodology to select a substitute or to guide the synthesis of a substitute, for one (or more) component(s) in an initial single phase or multiple phase system where the modified system containing the substitute component must exhibit at least one predetermined desired property. The invention may be applied to an initial single component system or an initial multi-component system. The invention also has applicability to select or to guide the synthesis of an operative component to effect the combination of a first and a second phase into a single phase system, dispersion or emulsion.

The term "component", as used in this application, means either a presently existing chemical, a synthesizable chemical or a hypothetical chemical structure. The term "system" means a collection of one or more components.

Mutate Sigma Profile In general, as indicated in the block 102 the first step of the method 100 is mutating the sigma profile of a component of the initial system to produce a corresponding hypothetical sigma profile of a candidate substitute component.

As discussed in the Background of this application, in COSMO methodology a component may be represented as a discrete surface, approximating a surface of salvation, embedded in a virtual conducting fluid. Each segment, or "charge tile", of this surface is characterized by its area, its elemental descriptors and the polarization charge on this segment. The sigma profile is the probability distribution of the sigma polarization charges on the component. A sigma profile may also comprise probability distributions considering additional properties of the segments or charge tiles such as the segments' elemental descriptors.

The sigma profile may be mutated in many different ways to carry out this step of the invention.

The mutation may be effected by altering the polarization charge of a single charge tile or by altering the polarization charges on a collection of tiles. By way of examples, the magnitude of charge on a tile may be either increased or decreased. The fraction of tiles having positive charge, negative charge, and/or neutral charge may be either increased or decreased. Multiple modifications to the fractions may be tried simultaneously. The mutations may be selected in a way that conserves the total charge of the component or in a way that changes the total charge of the component. The mutations may increase, decrease or leave unaffected the total surface area or the total number of segments approximating the surface of salvation of the component.

The mutation may additionally or alternatively be effected by altering one or more elemental descriptors of the initial component. Mutations may be selected to modify any aspect of the elemental descriptor to one or more segments. Mutations may be taken randomly from a library of single mutation methods or selected in groups of mutation methods to emulate collective fragments of molecular building blocks. Thus, the mutations represent the identifiable substitution of atoms, groups of atoms, molecular fragments, ligands, molecules, parts of surfaces and/or parts of crystals.

Mutations may be selected in a random, unbiased way. Mutations may be selected in a biased way to attempt more of one type of mutation more frequently than another type of mutation.

The net result of the mutation of the sigma profile of the component of the initial system is to produce a hypothetical sigma profile of a candidate substitute component for a modified system.

Compute Property The next step of the method 100 is indicated in the block 106. In this step the value of a selected property of a modified system that contains the candidate substitute component represented by the hypothetical sigma profile is computed.

To compute the value of the selected property of the modified system the sigma profile of the component or components of the system is(are) compressed into an imaginary phase and the overall interaction energies of the contacted sigma profiles are calculated. From the statistical mechanics of the interaction energies, selected thermodynamic properties can be calculated.

Any thermodynamic property that can be computed or correlated to the COSMO method can be selected. Properties that are currently known to be computed from the COSMO model or correlated with the COSMO model include:

free energy of mixing, heat of mixing, entropy of mixing, enthalpy of mixing, activity coefficient, chemical potential, vapor pressure, vapor-liquid equilibrium coexistence, liquid-liquid coexistence, gas solubility in liquids, liquid solubility in liquids, Henry's law constant, boiling point, melting point, viscosity, density, partition coefficient of a solute between two or more phases, pKa, diffusivity, surface tension, Helmholtz energy of mixing, and Gibbs energy of mixing.

It is also possible to correlate other properties with a COSMO model such as:

force of adhesion, heat capacity, thermal conductivity, modulus, thermoelectric constant, magnetic susceptibility, color, light transmissivity, light absorptivity, light reflectivity, mechanical strength, binding energy, Joule-Thompson coefficient, permeability, dielectric constant, azeotropic composition, crystal structure, refractive index, and contact angle.

As other properties are able to be correlated with a COSMO model these properties may also be used.

The applicability of the invention to single or multi-component and/or single or multiple phase systems follows from the ability of the COSMO methodology to calculate the thermodynamic equilibrium, transport or reaction properties of all of these systems.

The invention is not limited to the selection of properties of simple chemicals. The invention may be used to find the optimal length and sequence of monomers forming a macromolecule or polymer. The monomers may be synthetic in origin, such as styrene, acrylic acid, or vinyl acetate. The monomers may be amino acids, sugars or nucleotides which form proteins/polypeptides, carbohydrates and DNA/RNA, respectively. In such cases a selected component as a homopolymer may serve as the starting point and the monomer units are mutated into new repeat units, such as mutating the sigma profiles of amino acids to form new polypeptides/proteins.

It should be understood that the invention is not limited to the evaluation of only one selected property of a modified system. Plural (two or more) selected properties of a modified system that contains the candidate substitute component(s) represented by the hypothetical sigma profile(s) may be computed.

It should be understood that in some problems it is beneficial to select only one candidate component for mutation for achieving the modified selected thermodynamic property(ies). However, as noted, the invention is not limited to the choice of only one candidate component. The invention can be applied to multiple components in a multi-component system so that mutations are made sequentially to one component at a time or so that mutations are made in parallel to two or more components at a time before the selected thermodynamic property(ies) are assessed.

Compare to Reference Next, the calculated value of the thermodynamic property of the modified system having the component with the mutated sigma profile is compared to a predetermined reference value for the property. This action is indicated in the block 110.

As suggested in block 114 the reference value (goal) for the comparison may be based upon either a desired value for the selected property in the modified system or the initial value of the selected property in the initial system.

Accept or Discard Mutation As indicated in the block 122, a predetermined acceptance standard (indicated by the block 118) is next used to evaluate the results of the comparison 110 and to determine whether the hypothetical sigma profile produced as a result of the mutation (block 102) should be accepted or discarded. If the mutation is discarded the last-previous sigma profile is preserved.

The acceptance standard may be a simple decision standard or a Metropolis standard.

In a simple decision standard the mutation is either accepted if the comparison (110) is improved and/or unchanged, or rejected if the comparison (110) is decreased and/or unchanged.

By contrast, if a Metropolis standard is used the mutation is either accepted if the comparison (110) is improved and/or unchanged or accepted with a predetermined probability if the comparison is decreased. The predetermined probability may be a decreasing function of the magnitude of decrease in the comparison.

Repetition To Finishing Criterion As suggested by the decision block 128, steps 102 through 122 are repeated either for a predetermined number of repetitions or until the results of the comparison 110 of the selected property of the modified system and the reference value 114 meets a predetermined finishing criterion (indicated by the block 130). Each repetition is performed using either the currently-accepted sigma profile or the preserved (last-previous) sigma profile, as discussed in connection with the block 122.

The predetermined finishing criterion may take a variety of forms.

The predetermined finishing criterion 130 may be defined as the attainment of a predetermined value for the property.

The finishing criterion 130 may be just a simple improvement by some predetermined selected amount $\in$ (epsilon) over the initial value of the property.

When the goal is an improvement relative to the initial value of the selected property, it may not be necessary to prespecify the goal. It is sufficient to begin and to keep improving without predetermining in advance the extent of the improvement. In other instances a specific numerical value for the magnitude of the improvement may be set.

In other cases it may be desirable to set a specific, numerical value of the selected thermodynamic property. For example, if it is desired that a molecule boil at 100° C., that actual numerical value of that thermodynamic property is selected as the reference value, not any higher and not any lower. The finishing criterion may also be defined as a value lying within a predetermined range either above and/or below the desired value.

In cases where multiple properties are considered, the comparison of the computed values to the reference value and the finishing criterion may be formulated as a combination of improving one or more properties and/or attaining one or more properties with desired ranges. The finishing criterion may be described mathematically as an objective function which assigns a numerical result to the extents of improvement or approach to the desired properties.

An objective function allows improvements in either one or more properties to be weighted. As a generalized treatment consider a general objective function, f.

In the simplest case suppose it is desired only to increase the value of property p1 from its initial value p10. An objective function is constructed, such as the function:

$$f = c1*(p1-p10)$$

where c1 is a positive constant.
It may be appreciated that the value of f increases when the property value p1 is increased from p10 and the value of f decreases when the property value is less than p10.

If it is desired to decrease property p1 to be much less than its initial value p10, then the constant c1 may be made a negative number (e.g., −1) and still seek to maximize the objective function f in the selection decision.

Consider as another instance a compound having two properties p1 and p2. It is desired to increase these properties above their initial values p10 and p20, respectively. An agglomerate objective function may be created, such as the function:

$$f = c1*(p1-p10) + c2*(p2-p20),$$

where c1 and c2 are constants chosen to weight the improvements in the properties p1 and p2 relative to each other.

For example, if it is desired to emphasize increases in property p1 to a greater extent than increases in property p2, then constant c1 is made much larger than c2, e.g. c1=10 and c2=1. This has the effect of allowing even small decreases in c2 if a mutation makes a compensatingly larger increase in c1.

This same idea can be generalized to "n" number of components, with the function f as:

$$f = \sum_{l=1}^{n} c_l * (p_l - p_l^0).$$

This can be generalized to even more than one component since the properties pI and p10 can be computed as values from either single component values or combinations of component property values.

Types of expressions other than linear combinations of different properties can be used for objective functions. The selection of objective function is chosen merely to accomplish the desired solution to an individual problem and the use of objective function is a well-established, well-known practice in the science and art of optimization problems.

When the results of the comparison meet the predetermined finishing criterion the desired value of the selected property(ies) has(have) been obtained or after a predetermined number of repetitions have been attempted. Since any or all of these mutations may lead to a stable solution of the desired thermodynamic property, there may be many mutations of the initial sigma profile which lead to desirable modifications of the initial composition. The entire process of optimizing the desired thermodynamic property using random mutations may be repeated several times to look for multiple final answers, each having improvements in the selected thermodynamic property.

Repetitions may be initiated with the same or different identities of the selected initial component.

One potential use of the method of the present invention includes making repetitions of the same calculation. The exact same result each time may not be achieved because all the mutations are random (and necessarily different) during each repetition. The point is that the exact same starting compounds in the initial system may be used for each repetition. However, a repetition can change the initial component that starts getting mutations. For example, repetitions may be run using (A+B), (A'+B), (A"+B), (A'"+B), wherein A, A', A", A'" are each different starting molecules (each having unique sigma profiles).

It should also be understood that in those instances where, for whatever reason, the predetermined finishing criterion is not attained, useful information regarding a substitute of a component is nevertheless obtained. For example, in a situation where the process is truncated after a predetermined number of repetitions have been attempted (where the number of repetitions is determined by the amount of computational and other resources desired to be invested) it may be concluded that a particular property cannot be further improved. This is itself useful information.

Identify Substitute As indicated in block 134, it now remains to identify a component that exhibits a sigma profile corresponding to the mutated sigma profile of the candidate component that produces a modified system having the modified selected thermodynamic property(ies) that meets the predetermined finishing criterion. This may be accomplished in several potentially important ways.

First, a substitute component having essentially the desired sigma profile may be known. Thus, it is advantageous to keep of library database of sigma profiles of known chemicals.

Alternatively, molecular modifications with molecules with known sigma profiles may be required. In other words, it may be necessary to modify known components to obtain the desired sigma profile.

A chemical substitution or modification to a known molecule may be made and the sigma profile of this new molecule computed and compared to the desired sigma profile. Alternatively, it may be preferred to combine the sigma profiles of known molecular fragments such that the sum of the fragments' sigma profiles adds to the desired sigma profile. Any amalgamation of these fragments may be a suitable identification of the desired chemical component.

A substitute component having a sigma profile that corresponds to the sigma profile of that candidate substitute component that produces a modified system having a value of the selected property that meets the predetermined finishing criterion may be synthesized using any of a variety of known apparatus or a variety of known chemistries. For example, peptide synthesizers and nucleic acid synthesizers are available for custom peptide synthesis and custom DNA synthesis. Known chemistries for polymerizing synthetic polymers of specific monomer sequences include group transfer polymerization methods, RAFT polymerization methods, and living ionic polymerizations methods.

As alluded to earlier the method described above may be for single phase systems or appropriately adapted for use in selecting at least one substitute component for a multiple phase systems. By "phase" it is meant a homogeneous, physically distinct, and mechanically separable portion of matter present in a non-homogeneous physical-chemical system or an individual or subgroup distinguishably different in appearance or behavior from the norm of the group to which it belongs.

Thus, the invention may be applied to select at least one substitute component of an initial solution to produce a modified solution having at least one improved selected thermodynamic property. The initial solution has at least a first and a second initial component, each initial component having a predetermined, associated sigma profile.

The method of the present invention is useful is the field of liquid-liquid extraction. In this case multiple goals of thermodynamic properties need to be satisfied simultaneously. In liquid-liquid extraction, it is frequently desired to increase the solubility of a solute in a first solvent of a system while decreasing the solubility of the same solute in a second solvent. These questions may be addressed with the method of the present invention by defining an appropriate thermodynamic property defined as the difference of solubilities in the first and second solvent and then performing the method for the defined difference of solubilities property.

A program listing (pages A-1 through A-46) written in ANSI C programming language by which the present invention may be implemented is included herein following the description and preceding the claims. The program listing forms a part of this application.

EXAMPLES

The operation of the process in accordance with the present invention may be understood more clearly from the following examples.

Example 1

Solvent Selection for Chloroform

To demonstrate that the invention can find a compatible solvent for a known chemical to form a single phase, I have used the invention to find a compatible solvent for chloroform. I began by selecting a trial solvent hexane, which I knew is not a good solvent for chloroform because the two compounds form two separate phases when combined. I selected the free energy of mixing as the selected thermodynamic property and I wished to find a substitute for hexane which provides a negative value for the free energy of mixing with chloroform. COSMO calculations were made for chloroform and hexane to solve for their sigma profiles. Here I selected sigma profiles comprising polarization charges. I calculated the free energy of mixing with chloroform and hexane of this original mixture. The hexane sigma profile was mutated as discussed in connection with block 102 of FIG. 2.

A mutation comprised at least one and as many as four random changes to the sigma distribution by adding a random small fraction of charges of random polarization. A mutation also comprised one additional change to the sigma profile to ensure the aforementioned random changes conserve the neutral overall charge of the solvent. The mutation scheme also allowed for a net addition or subtraction of overall molecular area as charges are added or subtracted, respectively. After the sigma profile of the hexane component was mutated, the free energy of mixing for the trial component with chloroform was computed. If the free energy of mixing was improved by a decrease in its value, then the mutation was accepted and the sigma profile was retained. If the new free energy of mixing was the same or increased, then the mutation was discarded and the previously recorded sigma profile was preserved. This process was repeated until the free energy of mixing was less than −3 kcal/mol. Restarting with the original hexane trial component, the process of making random mutations to the sigma profile as described was repeated five more times, each time stopping using the same criterion. Upon inspecting a selected best mutated solvent I found that the number of neutral and near-neutral polarization charges had been decreased while there was a peak in polarization charges near −0.5 e/nm² and small peak in the polarization charges near about 1.3 e/nm². There was also a net loss in molecular area so that the sigma distribution was very similar to that of the acetone. I calculated the free energy of mixing between chloroform and acetone and verified that the free energy of mixing was better (more negative) than that calculated for chloroform and hexane. Hence I had designed a suitable solvent for chloroform using the invention.

The program listing included herein on pages A-1 through A-46 (following the description and preceding the claims) was used to implement this Example.

Example 2

Solvent Selection for Phenol (Prophetic)

To demonstrate that the invention can find an improved solvent for a known chemical to form a single phase, I use the invention to find an improved solvent for phenol. I begin by selecting water as a trial solvent which I know is only partially miscible with phenol. I select the free energy of mixing as the selected thermodynamic property and I wish to find a substitute for water which provides a more negative value for the free energy of mixing with phenol than with water. COSMO calculations are made for water and phenol to solve for their sigma profiles. Here I select sigma profiles comprising polarization charges. I calculate the free energy of mixing with phenol and water of this original mixture. The water sigma profile was mutated as discussed in connection with block 102 of FIG. 2. A mutation comprises at least one and as many as four random changes to the sigma distribution by adding a random small fraction of charges of random polarization. A mutation also comprises one additional change to the sigma profile to ensure the aforementioned random changes conserve the neutral overall charge of the solvent. The mutation scheme also allows for a net addition or subtraction of overall molecular area as charges are added or subtracted, respectively. After the sigma profile of the water component is mutated, the free energy of mixing for the trial component with phenol is computed. If the free energy of mixing is improved by a decrease in its value, then the mutation is kept and the sigma profile is recorded. If the new free energy of mixing is the same or increased, then the mutation is discarded and the previously recorded sigma profile is retained. This process is repeated until I observe no significant decreases in the free energy of mixing being made over the last hundred mutation attempts. Restarting with the original water trial component, the process of making random mutations to the sigma profile as described is repeated five more times, each time stopping using the same criterion. Upon inspecting a selected best mutated solvent I find that the number of neutral and near-neutral polarization charges has been greatly increased. Furthermore the hydrogen bonding peaks near about −1.6 and +1.8 e/nm$^2$ are replaced by peaks near about −0.5 and +1.3 e/nm$^2$, respectively. There is also a net gain in molecular area so that the sigma distribution is very similar to that of the acetone. I calculate the free energy of mixing between phenol and acetone and verify that the free energy of mixing is better (more negative) than that calculated for phenol and water. Hence I have now designed a more suitable solvent for phenol using the invention.

The program listing included herein on pages A-1 through A-46 (following the description and preceding the claims) is used to implement this Example.

Example 3

Selection of a Chemical by Boiling Point (Prophetic)

To demonstrate that the invention can find a suitable chemical based on a desired two phase property, I use the invention to find a solvent which boils near −160° C. within ±2° C. I begin by selecting a trial solvent hexane, which I know boils at +69° C. I select the temperature at which the liquid exerts an equilibrium vapor pressure of 1 atmosphere as the selected thermodynamic property and I wish to find a substitute for hexane which provides a boiling point value as −160° C. within ±2° C. COSMO calculations are made for hexane to solve for the sigma profile. Here I select a sigma profile comprising polarization charges. I calculate the vapor pressure of hexane at −160° C. of this original component. The hexane sigma profile was mutated as discussed in connection with block 102 of FIG. 2.

A mutation comprises at least one and as many as four random changes to the sigma distribution by adding a random small fraction of charges of random polarization. A mutation also comprises one additional change to the sigma profile to ensure the aforementioned random changes conserve the neutral overall charge of the solvent. The mutation scheme allows for a net addition or subtraction of overall molecular area as charges are added or subtracted, respectively. After the sigma profile of the hexane is mutated the vapor pressure is computed at −160° C. If the vapor pressure is brought closer to 1 atmosphere, then the mutation is kept and the sigma profile is recorded. If the vapor pressure is the same or if the vapor pressure is further away from the 1 atmosphere target, then the mutation is discarded and the previously recorded sigma profile is retained. This process is repeated until I observe the computed vapor pressure is brought within ±0.15 atm of the target 1 atm value. Restarting with the original hexane trial component, the process of making random mutations to the sigma profile as described is repeated five more times until I observe the computed vapor pressure is brought within ±0.15 atm of the target 1 atm value. Upon inspecting a selected best mutated trial I find that the number of neutral and near-neutral polarization charges has been decreased while there are now two peaks in polarization charges, one near −0.35 e/nm$^2$ and another near about 0.3 e/nm$^2$. Also the surface area of the best mutated trial has decreased substantially so that the sigma distribution is very similar to that of the methane. I calculate the vapor pressure of methane at −160° C. and verify that the vapor pressure is close to 1.12 atm. I calculate the temperature at which the vapor pressure equals exactly 1 atm and find a value of about −161° C., which falls within the ±2° C. tolerance of the desired −160° C. Hence I have now designed a suitable solvent having the desired boiling point using the invention.

The program listing included herein on pages A-1 through A-46 (following the description and preceding the claims) was used to implement this Example.

Example 4

Separation of CH$_2$F$_2$ and CHF$_2$CF$_3$ by an Ionic Liquid

A common refrigerant R-410A is an equimolar mixture of CH$_2$F$_2$ and CHF$_2$CF$_3$. The separation of these two components was desired using an extractive distillation process. Here I wished to select an extracting chemical component which has high solubility for CH$_2$F$_2$ and low solubility for CHF$_2$CF$_3$. I selected an extractive distillation process running at 10 atm pressure and enough absorber plates to accept the mixture at 10° C. and provide a condenser stream of purified CHF$_2$CF$_3$ at 13° C. and mixture of extractant and CH$_2$F$_2$ from the reboiler at 126° C. The CHF$_2$CF$_3$ was to be recovered from the extractant by flashing into the vapor phase at reduced pressure. The extractant was to be recycled back into the top of the absorber column. The initial trial extractant was an ionic liquid of butylmethyl imidazolium iodide. I selected the iodide anion as the trial component in the mixture to mutate to improve the separation process efficiency. I selected the measure of separation efficiency as the partition coefficient, being the solubility of CH$_2$F$_2$ in the extractant divided by the solubility of CHF$_2$CF$_3$ in the extractant, at 13° C. I sought to improve the process by finding the best possible separation of the CH$_2$F$_2$ and CHF$_2$CF$_3$ for a given number of equilibrium plates in the extractive distillation process by finding substituent(s) for the iodide anion which has the largest improvement in partition coefficient relative to our initial trial extractant. COSMO calculations were made for all chemicals to solve for their sigma profiles. Here I selected sigma profiles comprising polarization charges. I calculated the partition coefficient of this original mixture at 13° C.

The iodide anion sigma profile was mutated as discussed in connection with block 102 of FIG. 2. A mutation comprised at least one and as many as four random changes to the sigma distribution by adding a random small fraction of charges of random polarization. A mutation also comprised one additional change to the sigma profile to ensure the aforementioned random changes conserve the −1 overall charge of the iodide anion. The mutation scheme allowed for a net addition or subtraction of overall molecular area as charges were added or subtracted, respectively. After the sigma profile of the iodide anion was mutated the partition coefficient was computed. If the new partition coefficient was improved by an increase in its value, then the mutation was kept and the sigma profile was retained. If the new partition coefficient was the same or decreased, then the mutation was discarded and the previously recorded sigma profile was retained. This process was repeated until I observed no significant increases in the partition coefficient being made over the last hundred mutation attempts. Restarting with the original iodide trial component, the process of making random mutations to the sigma profile as described was repeated five more times, each time stopping after no new significant improvement was noted in the partition coefficient after a hundred mutation attempts. Upon inspecting a selected best mutated anion I found that the number of neutral and near-neutral polarization charges had been increased so that the sigma distribution was very similar to that of the acetate anion. I calculated the partition coefficient in butylmethyl imidazolium acetate and verified that the partion coefficient was better than that calculated for butylmethyl imidazolium iodide. Hence I had provided an improved process solvent for the separation using the invention.

The program listing included herein on pages A-1 through A-46 (following the description and preceding the claims) was used to implement this Example.

Example 5

Absorbent Design for an Absorption Cooling Process

An absorption cooling process (see for example A. Yokozeki, Applied Energy, 2005, Vol 80, p 383) was desired using ammonia as the refrigerant and an ionic liquid as the absorbent. The generator was to be run at a temperature of 100° C. and pressure of 15.6 bar. The condenser was to be run at a temperature of 40° C. and pressure of 15.6 bar. The evaporator was to be run at a temperature of 10° C. and a pressure of 6.15 bar. The absorber was to be run at a temperature of 40° C. and a pressure of 6.15 bar. The trial absorbent was an ionic liquid of butylmethyl imidazolium hexafluorophosphorus. I selected the hexafluorophosphorus as the trial component in the mixture to mutate to improve the cooling process efficiency, as measured by the coefficient of performance which is proportional to the quantity:

$$g(x_{absorber} - x_{generator})/(1 - x_{generator})$$

where $x_{absorber}$ is the mole fraction solubility of ammonia in the ionic liquid at the absorber's temperature and pressure and $x_{generator}$ is the mole fraction solubility of ammonia in the ionic liquid at the generator's temperature and pressure.

I selected the thermodynamic property to be g and I wished to mutate the anion component to achieve the largest possible value of g. I computed the polarization profile sigma profiles of ammonia, butylmethyl imidazolium and hexafluorophosphorous and computed an initial value of g. The sigma profile of the hexafluorophosphorus anion was mutated as discussed in connection with block 102 of FIG. 2. A mutation comprised at least one and as many as four random changes to the sigma distribution by adding a random small fraction of charges of random polarization. A mutation also comprised one additional change to the sigma profile to ensure the aforementioned random changes conserve the −1 overall charge of the hexafluorophosphorus anion. The mutation scheme allowed for a net addition or subtraction of overall molecular area as charges were added or subtracted, respectively. After the sigma profile of the hexafluorophosphorus anion was mutated the value of g was computed. If the new value of g was improved by an increase in its value, then the mutation accepted and the sigma profile was retained. If the new value of g was the same or decreased, then the mutation was discarded and the previously recorded sigma profile was preserved. This process was repeated until I observed no significant increases in the partition coefficient being made over the last hundred mutation attempts. Restarting with the original hexafluorophosphorous trial component, the process of making random mutations to the sigma profile as described was repeated five more times, each time stopping after no new significant improvement is noted in the value of g after a hundred mutation attempts. Upon inspecting a selected best mutated anion I found that the number of neutral and near-neutral polarization charges had been increased so that the sigma distribution was very similar to that of the acetate anion. I calculated the value of g in butylmethyl imidazolium acetate and verified that the value of g was better than that calculated for butylmethyl imidazolium hexafluorophosphorus. Hence I had provided an improved absorbent for the absorption cooling process using the invention. Upon inspecting another of the best mutated anions I found that the number of positive polarization charges had been increased and a large peak of negative polarization charges was present, thus creating an anion with an appreciable dipole moment. The sigma profile was very similar to that of tetrafluoroethane sulfonic acid. calculated the value of g in butylmethyl imidazolium tetrafluoroethane sulfonate and verified that the value of f was better than that calculated for butylmethyl imidazolium hexafluorophosphorus. Hence I provided a second improved absorbent for the absorption cooling process using the invention.

The program listing included herein on pages A-1 through A-46 (following the description and preceding the claims) was used to implement this Example.

Example 6

Emulsifier for Acrylates in Water (Prophetic)

An emulsifier is desired for preparing an emulsion of butylacrylate in water. I select two thermodynamic properties to use to select a good emulsifier which will disperse droplets of the butylacrylate in water: I calculate the free energy of mixing between water and the hydrophilic head of the emulsifer and the free energy of mixing between butylacrylate and the hydrophobic tail of the emulsifier. I construct a sigma profile of the total emulsifier by adding the sigma profiles of the hydrophilic head segment and the hydrophobic tail segment. I select as an initial trial emulsifier 1-octanol which we divide in half, the n-heptane fragment, $CH_3(CH_2)_6$, is assigned as the trial hydrophobic tail and the methylene-ol fragment, $CH_2OH$, is assigned as the trial hydrophilic head. The sigma profiles of the head and tail segments are computed by computing the sigma profile of 1-octanol and dividing the charge segments therein into head and tail sigma profiles depending on whether a charge segment was derived from an atom in the head segment or from an atom in the tail segment. Starting with the trial head and tail segments from 1-octanol, the sigma profiles of the head and tail sections are mutated in two independent mutation processes, as discussed in connection with block 102 in FIG. 2. In each mutation process a mutation comprises at least one and as many as four random changes to the sigma distribution by adding a random small fraction of charges of random polarization. In each mutation process a mutation also comprises one additional change to the sigma profile to ensure the aforementioned random changes conserve the neutral overall charge of the fragment. In each mutation process the mutation scheme also allows for a net addition or subtraction of overall molecular area as charges are added or subtracted, respectively. After the sigma profile of the trial head component is mutated, the free energy of mixing for the trial head component with water is computed. If the free energy of mixing is improved by a decrease in its value, then the mutation is accepted and the sigma profile is retained. After the sigma profile of the trial tail component is mutated, the free energy of mixing for the trial tail component with butylacrylate is computed. If the free energy of mixing is improved by a decrease in its value, then the mutation is accepted and the sigma profile is retained. This process is repeated for one thousand mutation attempts. Restarting with the original trial head and tail segments, the process of making random mutations to the sigma profile as described is repeated five more times. Upon inspecting a selected best mutated total emulsifier sigma profile, we find that the number of near-neutral tiles is greatly increased and new peaks at about $-2.4$ e/nm$^2$ and $+1.5$ e/nm$^2$ have been created so that the sigma profile is very similar to that of sodium laurylsulfate. Hence I have used the invention to provide an improved emulsifier for creating an emulsion of butylacrylate in water.

The program listing included herein on pages A-1 through A-46 (following the description and preceding the claims) is used to implement this Example.

Example 7

Design of a Binding Polypeptide (Prophetic)

A polypeptide dispersant is desired for dispersing carbon nanotubes in water. A library of sigma profiles for all 20 natural amino acids is constructed by performing COSMO calculations to compute the sigma profile of each amino acid using amine and carboxylic acid terminations for the amino acid monomer ends. The polarization charge segments corresponding to one hydrogen terminal are removed from the amine monomer end and to the acid hydrogen and oxygen are removed from the carboxylic acid monomer end for each of the amino acid sigma profiles. A sigma profile is also calculated for a 6.6 single wall carbon nanotube comprising 10 unit cells capped with hydrogens. The polarization charges of the hydrogen terminations for the single wall carbon nanotube and one ring of carbons at each end of the nanotube are removed from the sigma profile. A sigma profile for water is also constructed by performing COSMO calculations. I select two thermodynamic properties to use to select a good binding polypeptide which will bind to the nanotube and also form a dispersion in water: I calculate the free energy of mixing between water and polypeptide and the free energy of mixing between the single wall carbon nanotube and polypeptide. I construct a polypeptide sigma profile by adding eight identical sigma profiles of alanine from the aforementioned sigma profile library of amino acids. I select this polypeptide to be mutated one residue at a time to find a sequence of eight polypeptides which provide the smallest (most negative) free energy of mixing with the water sigma profile, so it is water soluble, and the smallest (most negative) free energy of mixing with the single wall carbon nanotube sigma profile, so it binds to the nanotube. A mutation comprises selecting one residue in the polypeptide sequence and substituting that residue's contribution to the polypeptide's total sigma profile with a sigma profile of another amino acid, chosen randomly. The total sigma profile of the new sequence is computed as the sum of the sigma profiles of each residue contained in the sequence and the two selected thermodynamic properties are calculated. If there is an improvement in both selected thermodynamic properties then the mutation is accepted and the polypeptide sequence is so adopted as the new sequence to mutate further. If there is an improvement in either of the selected thermodynamic properties then the mutation is accepted and the polypeptide sequence is so adopted as the new sequence to mutate further. If the mutation is discarded, then another residue is selected randomly to repeat the process illustrated in FIG. 2. This process is repeated for one thousand mutation attempts. Restarting with the original trial sequence, the process of making random mutations to the sigma profile as described is repeated five more times. Upon inspecting a selected best mutated sequence we find that the sequence is rich in histidine, tryptophan and phenylalanine. I compare this result with experimental data in which M13 phage display panning was performed on single wall carbon nanotubes (see C. K. Lau, Masters Thesis, MIT 2004) which also finds enhancement in histidine, tryptophan and phenylalanine residues. Hence I have provided an improved polypeptide which binds to single wall carbon nanotubes in water and validated the polypeptide composition with an independent experimental result.

The program listing included herein on pages A-1 through A-46 (following the description and preceding the claims) is used to implement this Example.

-o-0-o-

Those skilled in the art, having the benefit of the teachings of the present invention as hereinabove set forth may effect modifications thereto. It is understood that such modifications are to be construed as lying within the contemplation of the present invention, as defined by the appended claims.

What is claimed is:

1. A computer-implemented method of selecting an operative component to effect the combination of at least a first and a second immiscible phase into a single phase system, dispersion or emulsion,
    wherein the first and second phases are immiscible with each other,
    the method comprising the steps of:
    a) selecting a first candidate operative component and providing to a computing system in a machine readable form a sigma profile associated with the first candidate operative component and thereafter, performing on the computing system the following steps;
    b) computing the value of the free energy of mixing for the operative component and the components in the first and the second immiscible phases;
    c) if the free energy of mixing as computed in step b) is greater than zero, mutating the sigma profile of the first candidate operative component to define a hypothetical sigma profile of a candidate substitute operative component;
    d) computing the value of the free energy of mixing for the candidate substitute operative component and the components in the first and the second immiscible phases;
    e) repeating steps c) and d) either for a predetermined number of repetitions or until the value of the free energy of mixing of a combination of the candidate substitute operative component and the first and a second immiscible phases is less than zero, whichever first occurs; and, thereafter
    f) identifying a substitute material, if any, that exhibits a sigma profile corresponding to the mutated sigma profile of that candidate substitute operative component, if any, that produces a combination of the candidate substitute operative component and the first and a second immiscible phases having a free energy of mixing less than zero; and
    g) outputting from the computing system the identity of the substitute material, if any.

2. The method of claim 1, further comprising, after the outputting step g), the step of:
    physically producing a modified single phase system, dispersion, or emulsion comprising the substitute material and the at least the first and second immiscible phases, the substitute material effecting the combination of at least the first and second immiscible phases into the modified single phase system, dispersion, or emulsion.

3. A non-transitory computer readable medium having encoded thereon a computer-implemented method of selecting an operative component to effect the combination of at least a first and a second immiscible phase into a single phase system, dispersion or emulsion, wherein the first and second phases are immiscible with each other, the method comprising the steps of:

a) selecting a first candidate operative component and providing to a computing system in a machine readable form a sigma profile associated with the first candidate operative component and thereafter, performing on the computing system the following steps;

b) computing the value of the free energy of mixing for the operative component and the components in the first and the second immiscible phases;

c) if the free energy of mixing as computed in step b) is greater than zero, mutating the sigma profile of the first candidate operative component to define a hypothetical sigma profile of a candidate substitute operative component;

d) computing the value of the free energy of mixing for the candidate substitute operative component and the components in the first and a second immiscible phases;

e) repeating steps c) and d) either for a predetermined number of repetitions or until the value of the free energy of mixing of a combination of the candidate substitute operative component and the first and a second immiscible phases is less than zero, whichever first occurs; and, thereafter f) identifying a substitute material, if any, that exhibits a sigma profile corresponding to the mutated sigma profile of that candidate substitute operative component, if any, that produces a combination of the candidate substitute operative component and the first and a second immiscible phases having a free energy of mixing less than zero.

* * * * *